United States Patent [19]

Magori

[11] Patent Number: 4,656,384

[45] Date of Patent: Apr. 7, 1987

[54] ULTRASONIC DETECTION SENSOR IN HYBRID STRUCTURE WITH APPERTAINING ELECTRONIC CIRCUIT

[75] Inventor: Valentin Magori, Munich, Fed. Rep. of Germany

[73] Assignee: Siemens Aktiengesellschaft, Berlin and Munich, Fed. Rep. of Germany

[21] Appl. No.: 788,875

[22] Filed: Oct. 18, 1985

[30] Foreign Application Priority Data

Oct. 25, 1984 [DE] Fed. Rep. of Germany ....... 3439168

[51] Int. Cl.[4] ............................................. H01L 41/08
[52] U.S. Cl. .................................. 310/334; 310/337; 310/368; 310/340
[58] Field of Search ................................ 310/334-338, 310/340, 322, 323, 368; 73/632, 642, 644, 290 V; 367/155, 157, 162, 165; 340/603, 618, 621

[56] References Cited

U.S. PATENT DOCUMENTS

| | | | |
|---|---|---|---|
| 3,587,561 | 6/1971 | Ziedonis | 310/335 X |
| 3,944,994 | 3/1976 | Fanshawe | 340/621 X |
| 3,979,711 | 9/1976 | Maginness | 310/377 UX |
| 4,086,696 | 5/1978 | Ikuta | 310/340 X |
| 4,127,788 | 11/1978 | Daugherty | 310/334 X |
| 4,217,684 | 8/1980 | Brisken et al. | 310/334 X |
| 4,316,183 | 2/1982 | Palmer et al. | 340/621 |
| 4,549,107 | 10/1985 | Kaneko et al. | 310/335 X |
| 4,565,942 | 1/1986 | Sakai et al. | 310/337 |

FOREIGN PATENT DOCUMENTS 4515186  8/1967  Japan .................................... 310/337

OTHER PUBLICATIONS

Hybrid Linear and Matrix Acoustic Arrays—by M. Papplardo, *Ultrasonics*, Mar. 1981, pp. 81-86.

*Primary Examiner*—Mark O. Budd

[57] ABSTRACT

An ultrasonic detection sensor having an integrated structure and formed of a substrate such as used for thick film circuits on which is secured at least one ultrasonic transducer formed of a film packet having n piezo ceramic films and n+1 plastic films. One outermost plastic film layer is secured to the substrate, serving as a backing for the transducer, and a thick film electrical circuit is formed on the same substrate.

20 Claims, 8 Drawing Figures

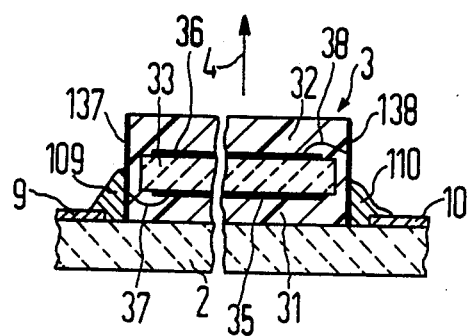
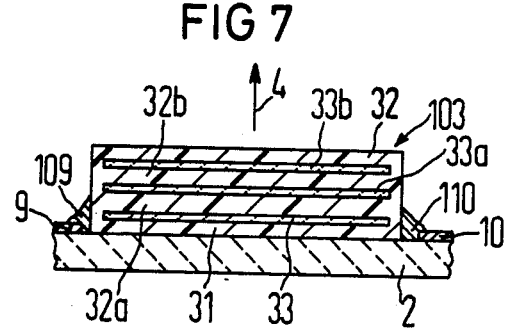

ULTRASONIC DETECTION SENSOR IN HYBRID STRUCTURE WITH APPERTAINING ELECTRONIC CIRCUIT

BACKGROUND OF THE INVENTION

1. Field of the Invention

The present invention relates generally to an ultrasonic detection sensor and more particularly to an ultrasonic transducer formed of alternating layers of piezo ceramic and plastic mounted on a thick film substrate.

2. Description of the Prior Art

It is known to use ultrasonic signals to detect distances between bodies. Generally, an ultrasonic transducer is mounted on one body to emit an ultrasonic signal which is reflected by a second body disposed at a distance from the first, after which the transit time of the reflected signal from the second body is evaluated. The emitting transducer and the receiving transducer can also be mounted separately from one another at respective first and second bodies disposed opposite one another; this, however, requires two separate transducers. Beside the bodies on which the transducers are mounted, there can also be other boundary surfaces reflecting the ultrasonic signal such as, for example, the surface of a liquid. This concept is used in liquid level detectors using ultrasonic signals, whereby an ultrasonic transmission is reflected back into the liquid at a surface or reflected back to the outside of the liquid from the surface. It is known, for example, to provide tank measuring apparatus, in particular for fuel tanks in motor vehicles. One of such tank measuring apparatus includes an ultrasonic transducer mounted at the bottom of a fuel tank to emit an ultrasonic signal that is reflected at the surface of the fuel situated in the tank and returned to a transducer (which may also be the transmitting transducer). Electronic circuitry for evaluating a signal from such tank measuring apparatus is also known as is shown in the laid open German Pat. No. OS 30 03 317.

When ultrasonic transducers are to be used in large numbers as, for example, in motor vehicles it is necessary to have transducers which are both effective as well as of simple and rugged construction. It is also desirable to provide transducers which are relatively inexpensive to manufacture.

SUMMARY OF THE INVENTION

It is an object of the present invention to provide an ultrasonic transducer of simple, rugged construction which is relatively inexpensive to manufacture. This and other objects are achieved in an ultrasonic sensor having a layered transducer portion mounted on a thick film substrate along with a thick film electrical circuit to drive the transducer. The layered ultrasonic transducer includes at least one layer of piezo ceramic and at least two layers of plastic material alternating therewith wherein one of said plastic layers is secured to the substrate and another, opposing one of said plastic layers is at an outside surface of the transducer. A plurality of such ultrasonic transducers may be provided on a single substrate and may include notches in a common piezo ceramic layer for acoustic decoupling between the individual transducers.

It is desirable for an ultrasonic transducer to have optimal acoustic resistance matching with the transmitting medium. The present invention provides the possibility of achieving acoustic resistance matching simply by means of changes in the plastic layer material. Furthermore, the present invention has a compact structure which not only enables integrated manufacturing methods to be used but reduces costs for the user when the device is installed.

The invention provides a substrate material which forms a hard acoustic mass as a backing. The actual ultrasonic transducer is composed of one or more wafers of piezo ceramic with plastic members applied thereto at the front and back sides and interleaved therewith. This composite forms a quarter wavelength transducer ($\lambda/4$) or, respectively, a $(2n+1\cdot\lambda/4)$ transducer. One surface of this composite transducer, also referred to as a film packet, is applied to the substrate and the other surface serves as the emission face which is adjoined by the sound propagation medium, preferably a liquid.

The present invention provides a means for achieving the greatest possible degree of acoustic matching wherein, insofar as possible, the mean value of the product of the velocity of sound in and the density of the transducer lies between or is equal to the corresponding mean product values of the substrate material and of the adjoining medium. This is achieved in a transducer formed of piezo ceramic film layer(s) and of plastic, or piezopolymer, film layers.

While a single ultrasonic transducer can be applied to a substrate as mentioned above, two transducers can also be applied to a single substrate, the first transducer being a transmission transducer and the second a reception transducer. The present invention also encompasses an ultrasonic array arrangement composed of a plurality of transducers which, while being secured to a single substrate, are functionally discrete and may be excited as a transmission transducer array according to known patterns, including producing selective directional transmission by varying the phase of the transmission across the array.

Yet a further feature of the present invention is to include the electronic evaluation circuit on the same substrate. This single piece arrangement needs only an external supply of power to provide a signal output which can be directly conducted to a display, such as a fuel gauge in an automobile dashboard.

DESCRIPTION OF THE DRAWINGS

FIG. 6 is an enlarged cross section of a portion of an acoustic transducer according to the principles of the present invention showing the electrical connections thereto.

FIG. 7 is a cross section of a multiple ceramic layered embodiment of an ultrasonic transducer according to the principles of the present invention.

DESCRIPTION OF THE PREFERRED EMBODIMENTS

Figure 1:
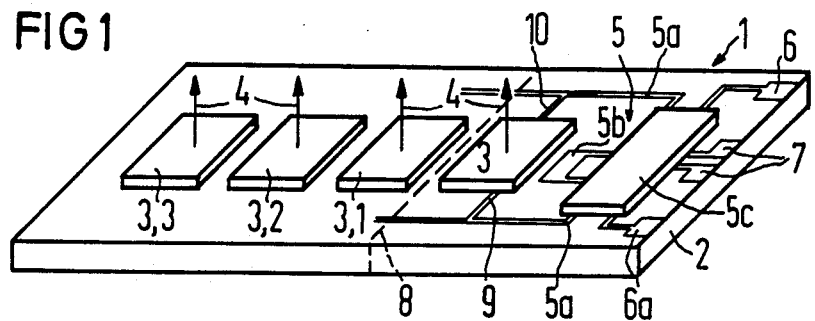
FIG. 1 is a perspective view showing an ultrasonic transducer array sensor according to the principles of the present invention.

In FIG. 1, an ultrasonic transducer sensor arrangement according to the present invention is shown generally at 1. The transducer arrangement 1 includes generally a substrate plate 2 and an array of ultrasonic transducers 3; 3,1; 3,2; 3,3 arranged thereon. More specifically, the substrate plate 2 is of a material such as sintered aluminum oxide or ceramic such as is used in thick film technology and includes the four ultrasonic transducers 3; 3,1; 3,2; 3,3 arranged in a single row. An emission direction of the ultrasonic signal is indicated at 4 for the individual transducer 3 and for the array arrangement comprising the transducers 3 through 3,3 when subject to equiphase excitation. An electrical circuit 5 is situated on the substrate plate 2 and is a thick film circuit including interconnects 5a, thick film components 5b, and additionally applied components 5c which may be in hybrid technology. Terminals 6 and 6a are provided for connection to a supply voltage and terminal 7 is provided as an output connection. The terminal 7 may either be a single lead or a dual lead terminal. The electrical circuit 5 as shown is designed so that it provides both emission excitation of the transducers 3 through 3,3 as well as the evaluation of the reflected signals received thereby.

While FIG. 1 shows an ultrasonic sensor 1 having a plurality of transducers 3 through 3,3, it is also possible to construct an ultrasonic sensor having only one transducer 3. A single transducer sensor is shown to the right of a dotted line 8 in FIG. 1 wherein the transducer 3 is used as both a transmitting and receiving transducer. The transducer 3 is secured on a common substrate 2 with the electrical circuit 5 as a hybrid structure and are connected to one another by lead lines or interconnects 9 and 10.

While FIG. 1 shows the electrical circuit 5 on the same side of the substrate 2 as the transducers, it is also foreseen to mount one or more of the ultrasonic transducers 3; 3,1; 3,2; and 3,3 on one side of the substrate plate 2 and to mount the electrical circuit 5 on an opposing side of the substrate plate 2.

Figure 2:
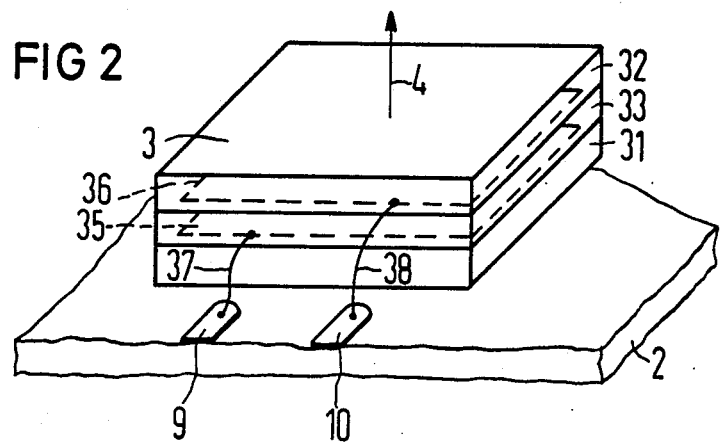
FIG. 2 is an enlarged perspective view of one ultrasonic transducer of FIG. 1.

FIG. 2 shows the layered construction of the transducer 3 employed in the present invention. The transducer 3 is composed of a piezo ceramic film or layer 33 adjoined by films or layers 31 and 32 of a material having a specific density, or gravity, of less than roughly 2 and which, in particular, can be carbon and/or silicon polymer plastics. Polymer ethylene, epoxide, and PVDF are examples of suitable plastics. The plastic also preferably surrounds the ceramic at the edges (see FIGS. 3, 6, and 7).

At its opposing surfaces, the ceramic film 33 includes electrode coatings 35 and 36. First and second electrically insulated conductors 37 and 38 connect the ceramic film 33 externally. The conductors 37 and 38, which are preferably stranded or unstranded wire, are connected to interconnecting leads 9 and 10 respectively, and thus to the electrical circuit 5.

To provide electrical shielding and for improving adhesion, the substrate plate 2 can be coated with an electrically conductive layer such as stoving metal or sputtered metal at the locations where the transducers 3; 3,1; 3,2; and 3,3 are applied.

Figure 3:
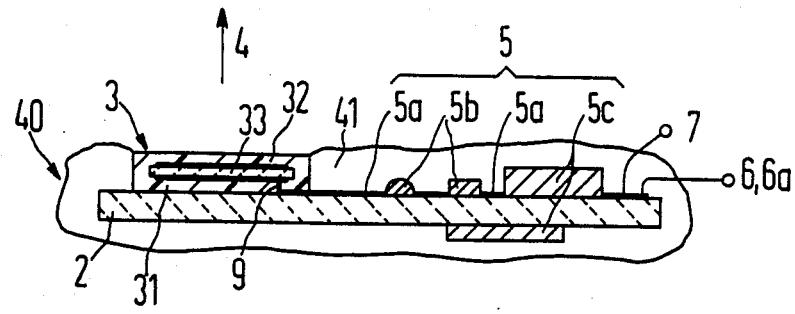
FIG. 3 is a lateral cross section of a single ultrasonic transducer sensor similar to that shown on the right in FIG. 1.

In the cross section of FIG. 3, a sensor 40 is shown similar to that portion of FIG. 1 to the right of line 8. A protective coating 41 is included on all sides of the sensor 40. The protective coating 41 is, for example, an immersion lacquer or a casing applied by means of whirl sintering. The upper surface of the transducer 3 is to be kept free of the casing material 41 to prevent attenuation of the sound emission 4. Protection of the transducer upper surface is not generally required since it is already composed of a plastic film layer 32.

The sensor 40 of FIG. 3 is quite versatile and can be used and operated inside of liquid containers, such as being immersed in the liquid. It is protected from reactive and/or solvent liquids by the casing 41, which may be of such suitable protective materials as are well known.

Figure 4:
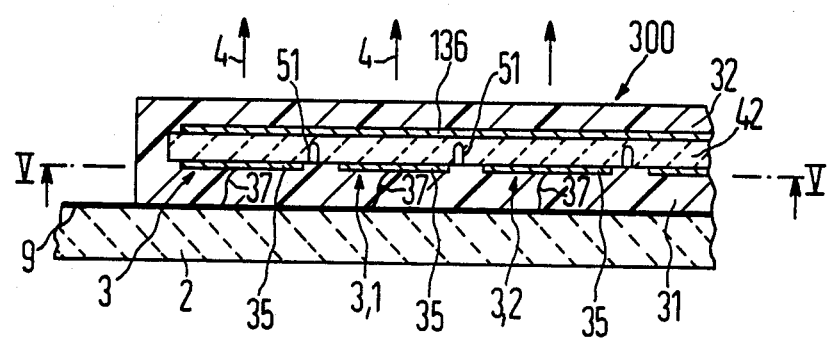
FIG. 4 is a cross section of a common ceramic embodiment of an ultrasonic transducer array according to the principles of the present invention.

Another embodiment of a transducer array 300 of the present invention is shown in FIG. 4. The transducer array 300 includes a substrate plate 2 on which the transducers 3; 3,1; and 3,2 are secured. Plastic film layers 31 and 32 envelope a single strip-shaped piezo ceramic film 42. The individual transducers 3; 3,1; and 3,2 thus become integral components of the overall transducer array 300. Each of the transducers 3; 3,1; and 3,2 have respective electrode coatings 35 on the lower surface thereof while an opposite upper surface includes a single strip-shaped electrode coating 136 extending therealong which connects the transducer 3; 3,1; and 3,2 unipolarly to one another. By appropriate excitation via the leads 37, the individual transducers 3; 3,1; and 3,2 can be excited to a prescribed operating mode of the array, which for example may include equiphase or different phase modes.

Figure 5:
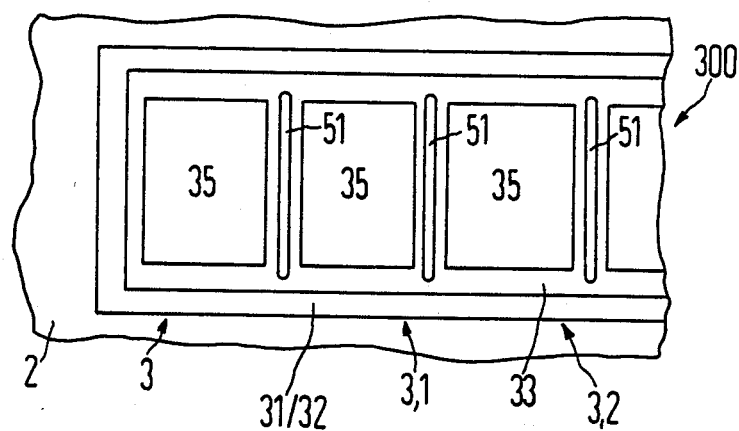
FIG. 5 is a plan view from the bottom of the array shown in FIG. 4 taken along lines V—V.

The underside of the piezo ceramic strip 42 can be seen in FIG. 5. The individual transducer elements 3; 3,1; and 3,2 are ultrasonically decoupled from one another by incisions 51 at spaced locations along the piezo ceramic strip 42. As indicated by FIGS. 4 and 5, any number of transducer units may be included in an ultrasonic sensor array.

FIG. 6 illustrates one example of providing connections to the electrode coatings 35 and 36 of the piezo ceramic film 33 for the operation of the transducer 3. The piezo ceramic film 33 with its electrode coatings 35 and 36 are mounted on a portion of the substrate plate 2. Conductors 37 and 38, which are fine wires or stranded conductors, connect the electrode coatings 35 and 36 to end-face metallizations 137 and 138 on the transducer 3 or, more specifically, on its plastic film layers 31 and 32. The interconnecting leads 9 and 10 on the substrate plate 2 which provide for connection of the transducer 3 are electrically linked to the respective metallizations 137 and 138 by soldered connections 109 and 110, respectively. The provision of such soldered connections are known in the thick film circuit art and end-face metallizations are known in the context of plastic capacitors and the like.

A multi-layered embodiment of a transducer 103 of the present invention is shown in FIG. 7. This embodiment includes three piezo ceramic films 33, 33a and 33b superimposed one over another. Plastic film layers 31 and 32 are disposed at opposing outer surfaces of the transducer 103, while further plastic film layers 31a and 31b separate the piezo ceramic films 33, 33a and 33b from one another. Although not shown in FIG. 7, electrode coatings of the piezo ceramic films 33, 33a and 33b and their respective leads are provided analogous to FIG. 2. The operation of the multilayered transducer 103 of FIG. 7 is fundamentally the same as that of the transducer 3 of FIG. 2. A multilayer transducer analogous to FIG. 7 may also be constructed in an array in accord with FIGS. 4 and 5.

The piezo ceramic films 33, 33a and 33b generally have a thickness dimension of less than 0.5 mm. The thickness dimension of the plastic film layers range within an order of magnitude of the ceramic film thickness although plastic film up to 10 times thicker than the ceramic film may be used.

Figure 8:
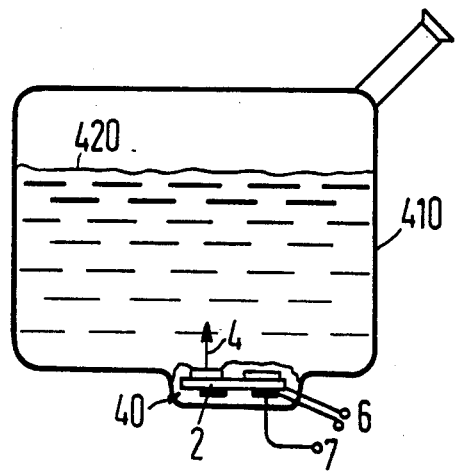
FIG. 8 is a cross section of a tank showing the ultrasonic transducer sensor of FIG. 3 used therein as a level sensor.

A sensor 40 of the present invention is shown in FIG. 8 used as a liquid level sensor in a tank 410, such as a fuel tank. The sensor 40 emits an ultrasonic signal in the direction indicated at 4, which is reflected at the liquid surface 420 and, in turn, received by the sensor 40; the transition time being a measure of the fluid level within the tank 410.

It is apparent from the foregoing specification, that the invention is susceptible to being embodied with various alterations and modifications which may differ particularly from those that I have described in the preceding specification and description. It should be understood that I wish to embody within the scope of the patent granted hereon all such modifications as reasonably and properly come within the scope of my contribution to the art.

I claim:

1. An ultrasonic detection sensor, particularly for use in liquids, comprising:
   a thick film substrate plate as a hard acoustic mass forming a backing;
   a thick film electrical circuit formed on said substrate and including connection terminals;
   at least one layered ultrasonic transducer formed of alternating thick film layers including at least one thick film applied layer of piezo ceramic and at least two thick film applied layers of plastic material alternating with said at least one piezo ceramic layer, said plastic material having a specific gravity of less than 2, one of said plastic thick film layers forming an outside surface of said transducer and an opposing one of said plastic thick film layers being secured to said substrate.

2. A sensor as claimed in claim 1, wherein said thick film electrical circuit and said at least one layered ultrasonic transducer are applied to the same surface side of said substrate.

3. A sensor as claimed in claim 1, wherein said thick film electrical circuit and said at least one layered ultrasonic transducer are applied to opposing surface sides of said substrate.

4. A sensor as claimed in claim 1, wherein said thick film electrical circuit is a transmission and reception circuit.

5. A sensor as claimed in claim 1, further comprising a plurality of ultrasonic transducers forming a transducer array on said substrate.

6. A sensor as claimed in claim 1, wherein said plastic film layers extend beyond the outer edges of said at least one piezo ceramic film layer.

7. A sensor as claimed in claim 1, further comprising metallizations between said at least one piezo ceramic film layer and respective adjoining ones of said plastic film layers.

8. A sensor as claimed in claim 1, wherein said plastic layers are connected to one another at the edges of said at least one piezo ceramic layer to form end faces, and further comprising: metallizations at said end-faces of said ultrasonic transducer; electrode coatings on opposing faces of said at least one piezo ceramic layer; fine conductors connecting said electrode coating to said end face metallizations; interconnecting leads provided on said substrate; and solder connections between said metallized end-faces and said interconnecting leads for supplying power to and receiving signals from said ultrasonic transducer.

9. A sensor as claimed in claim 1, further comprising an array of ultrasonic transducers formed of a single strip-shaped piece of piezo ceramic film having notches therein for acoustic decoupling between individual portions of said piezo ceramic film corresponding to individual transducers of said array, a single electrode coating extending along a first surface of said single piece of piezo ceramic film, and a plurality of electrode coatings applied to respective ones of said individual transducers at an opposite second surface of said single piece of piezo ceramic, said second surface being applied to said plastic layer secured to said substrate.

10. A sensor as claimed in claim 1, wherein said plastic film layers are of a hydrocarbon polymer.

11. A sensor as claimed in claim 1, wherein said plastic film layers are of a hydrosilicon polymer.

12. A sensor as claimed in claim 1, wherein said sensor is used for ultrasonic emission in a liquid.

13. A sensor as claimed in claim 2, wherein notches extend across only part of the width of said at least one film layer of piezo ceramic film.

14. A sensor as claimed in claim 2, further comprising:
   a pair of ultrasonic transducers, a first of said pair being a transmitting transducer, and a second of said pair being a receiving transducer.

15. An ultrasonic detection sensor, particularly for use in liquids, comprising:
   a thick film substrate being a backing;
   a thick film electrical circuit formed on said substrate and including connection terminals;
   at least one layered ultrasonic transducer including at least one film layer of piezo ceramic and
   at least two film layers of plastic material alternating with said at least one piezo ceramic layer, said plastic material having a specific gravity of less than 2, one of said plastic material layers being an outside surface of said transducers and an opposing one of said plastic material layers being secured to said substrate;
   said at least one layered transducer having a lower mean value of the product of the speed of sound therein and the density thereof than a corresponding mean product value of said substrate.

16. An ultrasonic detection sensor particularly for use in liquids comprising:
   a thick film substrate being a backing;
   a thick film electrical circuit formed on said substrate and including connection terminals;
   at least one layered ultrasonic transducer including at least one film layer of piezo ceramic and at least two film layers of plastic material alternating with said at least one piezo ceramic layer, said plastic material having a specific gravity of less than 2, one of said plastic material layers being an outside surface of said transducer and an opposing one of said plastic material layers being secured to said substrate;
   said at least one layered transducer having a mean value of the product of the speed of sound therein and the density thereof substantially equal to the mean value of a corresponding mean value of the product value of said substrate, and the product value of the medium through which said transducer propogates sound emissions.

17. An ultrasonic sensor, comprising:
a substrate plate for use in thick film technology; an electrically conductive layer covering predetermined portions
of said substrate plate for electrical shielding; at least one ultrasonic transducer secured to said predetermined portions of said substrate plate, said ultrasonic transducer including:
at least one thick film layer of piezo ceramic having a thickness of less than 0.5 mm,
at least two thick film layers of plastic alternating with said at least one piezo ceramic layer, one of said plastic layers being secured to said substrate and an opposing one of said plastic layers being an emitting face of said transducer, said plastic layers extending beyond the edges of said at least one piezo ceramic layer and connected to one another around said edges, each of said plastic layers having a thickness of no greater than ten times the thickness of said piezo ceramic layer,
metallized portions at opposing faces of said at least one piezo ceramic thick film layer,
conductors connected to said metallized portions and extending externally of said transducer and said ultrasonic transducer forming a $$\frac{(2n+1)\lambda}{4}$$

transducer for n=0, 1, 2, . . .

18. A sensor as claimed in claim 5, further comprising:
metallized end faces on said transducer, said conductors being connected to said metallized end faces.

19. An ultrasonic detector sensor, particularly for use in liquids, comprising:
a thick film substrate being a backing;
a thick film electrical circuit formed on said substrate and including connection terminals at least one layered ultrasonic transducer including at least one film layer of piezo ceramic and at least two film layers of plastic material alternating with said at least one piezo ceramic layer, said plastic material having a specific gravity of less than 2, one of said plastic material layers being an outside surface of said transducer and an opposing one of said plastic material layers being secured to said substrate;
said at least one ultrasonic transducer being formed of a plurality of said piezo ceramic film layers interleaved with said plastic film layers to form a film packet having plastic film layers at opposing outside surfaces.

20. An ultrasonic detector sensor, particularly for use in liquids, comprising:
a thick film substrate being a backing;
a thick film electrical circuit formed on said substrate and including connection terminals at least one layered ultrasonic transducer including at least one film layer of piezo ceramic and at least two film layers of plastic material alternating with said at least one piezo ceramic layer, said plastic material having a specific gravity of less than 2, one of said plastic material layers being an outside surface of said transducer and an opposing one of said plastic material layers being secured to said substrate;
a protective casing enveloping said electrical circuit and said substrate and a portion of said ultrasonic transducer, one of said plastic film layers of said acoustic transducer opposite said substrate being free of said protective casing, and
said connection terminals being conducted through said protective casing.

* * * * *